United States Patent [19]
Kerb et al.

[11] Patent Number: 4,871,725
[45] Date of Patent: Oct. 3, 1989

[54] 1-METHYL-15α-(1-OXYALKYL)ANDROSTA-1,4-DIENE-3,17-DIONES, PROCESSES FOR THEIR PRODUCTION, AND PHARMACEUTICAL PREPARATIONS CONTAINING THEM

[75] Inventors: Ulrich Kerb; Yukishige Nishino; David Henderson, all of Berlin, Fed. Rep. of Germany

[73] Assignee: Schering Aktiengesellschaft, Berlin and Bergkamen, Fed. Rep. of Germany

[21] Appl. No.: 157,568

[22] Filed: Feb. 19, 1988

[30] Foreign Application Priority Data

Feb. 20, 1987 [DE] Fed. Rep. of Germany ....... 3705990

[51] Int. Cl.[4] ........................... A61K 31/56; C07J 1/00
[52] U.S. Cl. .................................. 514/177; 260/397.3
[58] Field of Search ...................... 260/397.3; 514/177

[56] References Cited

U.S. PATENT DOCUMENTS 3,123,622 3/1964 Tweit ................................ 260/397.3
4,202,891 5/1980 Schroepfer et al. ................. 514/177
4,289,762 9/1981 Metcalf et al. .

FOREIGN PATENT DOCUMENTS 255272 6/1987 European Pat. Off. .
4529M 5/1965 France ................................. 514/177
4798M 10/1965 France ................................. 514/177

OTHER PUBLICATIONS

Taber's Cyclopedic Medical Dictionary, Edition 13, Illustrated, p. M-9.
Brodie, A. M., et al., "Studies on the Mechanism of Estrogen Biosynthesis is in the Rat Ovary,", *J. Steroid Biochem.*, 1976, vol. 7, pp. 787-791.

Primary Examiner—Douglas W. Robinson
Assistant Examiner—Joseph A. Lipovsky
Attorney, Agent, or Firm—Millen, White & Zelano

[57] ABSTRACT

1-Methyl-15α-(1-oxyalkyl)androsta-1,4-diene-3,17-diones of general Formula I

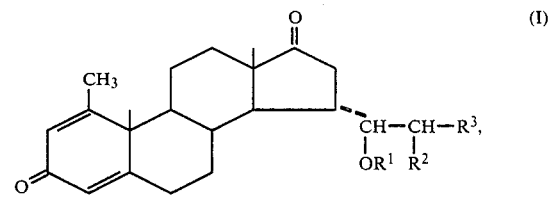

wherein
$R^1$ is a hydrogen atom or an acyl group of 1-10 carbon atoms,
$R^2$ is an $OR^4$, $NHR^5$ or an $S(O)_nR^6$ group, $R^4$ being straight- or branched-chain alkyl group of 1-10 carbon atoms, $R^5$ being an acyl group of 1-10 carbon atoms, $R^6$ being a straight- or branched-chain alkyl group of 1-10 carbon atoms or an aryl group of 6-10 carbon atoms,
$R^3$ is a hydrogen atom or a straight- or branched-chain alkyl group of 1-8 carbon atoms, and n is 0, 1 or 2, are suitable as inhibitors of estrogen biosynthesis for fertility control and for the treatment of diseases that are evoked by estrogens.

20 Claims, No Drawings

1-METHYL-15α-(1-OXYALKYL)ANDROSTA-1,4-DIENE-3,17-DIONES, PROCESSES FOR THEIR PRODUCTION, AND PHARMACEUTICAL PREPARATIONS CONTAINING THEM

BACKGROUND OF THE INVENTION

In pending application Ser. No. 925,955, filed Oct. 3, 1986, there are disclosed 1-methyl-15α-alkylandrosta-1,4-diene-3 17-diones of the formula

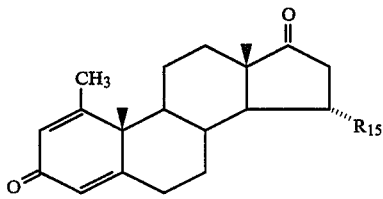

wherein $R_{15}$ is alkyl of 1-4 carbon atoms, alkyl substituted in the 1, 2 or 1 and 2 positions by hydroxy, $C_2$-$C_7$-alkanoyloxy or 1,2-isopropylidenedioxy.

The compounds are used in the inhibition of estrogen biosynthesis. In addition, pending application Ser. No. 152,222, a CIP of Ser. No. 925,955, discloses estrogen inhibitors of the above formula wherein $R_{15}$ is $C_{2-10}$-alkyl or $C_{2-10}$-alkyl substituted in the 1 and 2 position by two $C_{1-7}$-alkanoyloxy groups. The alkanoyloxy groups may be identical or different.

SUMMARY OF THE INVENTION

It is an object of the invention to provide improved estrogen inhibitors, having pharmaceutical utility.

Upon further study of the specification and appended claims, further objects and advantages of this invention will become apparent to those skilled in the art.

These objects have been satisfied by the provision of novel 1-methyl-15α-(1-oxyalkyl)androsta-1,4-diene-3,17-diones, processes for their production, pharmaceutical preparations containing them, and methods for their use in the production of medicinal agents.

The compounds of this invention are described by the Formula I

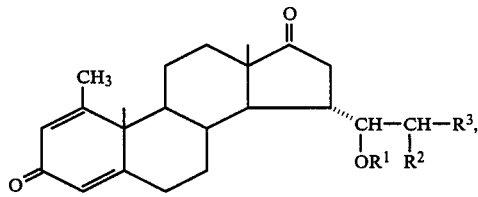

wherein
$R^1$ is a hydrogen atom or an acyl group of 1-10 carbon atoms,
$R^2$ is an $OR^4$, an $NHR^5$ or an $S(O)_n R^6$ group, $R^4$ being a straight- or branched-chain alkyl group of 1-10 carbon atoms, R5 being an acyl group of 1-10 carbon atoms, $R^6$ being a straight- or branched-chain alkyl group of 1-10 carbon atoms or an aryl group of 6-10 carbon atoms,
$R^3$ is a hydrogen atom or a straight- or branched-chain alkyl group of 1-8 carbon atoms, and n is 0, 1 or 2.

DETAILED DESCRIPTION

The acyl group $R^1$ contains 1-10 carbon atoms, and for example is alkanoyl. Acetyl, propionyl, isopropionyl and butyryl groups are preferred. $R^3$ is a straight- or branched-chain alkyl group and contains 1-8 carbon atoms; methyl, ethyl, propyl, butyl, isobutyl and pentyl are preferred.

The straight- or branched-chain alkyl group $R^4$ contains 1-10 carbon atoms; methyl, ethyl, propyl and isopropyl groups are preferred. The acyl group $R^5$, e.g. alkanoyl, contains 1-10 carbon atoms; acetyl, propionyl and isobutyryl groups are preferred. The straight- or branched-chain 1-10 carbon atom alkyl group or 6-10 carbon atom aryl group $R^6$ is preferably methyl, ethyl, propyl, isopropyl, phenyl, toluyl and naphthyl. Alkyl here and above can also be butyl, isobutyl, tertbutyl, pentyl, or isopentyl, or hexyl, heptyl, octyl or nonyl and their isomers.

It has now been found that the novel compounds of Formula I are aromatase inhibitors and inhibit estrogen biosynthesis.

Thus, it is shown, for example, in the so-called PMSG (pregnant mare's serum gonadotropin) test that, as compared with the conventional aromatase inhibitor 4-hydroxy-4-androstene-3,17-dione, the serum estradiol concentration is lowered to a greater extent with the compounds according to this invention.

Infantile female rats react to PMSG treatment with a uniformly increased steroid synthesis. The aromatase activity can be measured by the effect on PMSG-stimulated estrogen formation. J.Steroid.Biochem. 7, (1976),787. The anti-tumor activity in humans of compounds which have a positive effect in the PMSG-test is described in The Lancet, 1.Dec.1984, pages 1237-1239.

In the so-called PMSG test, 21-day-old female rats are pretreated every 2 days, in total seven times, with respectively 100 I.U. of PMSG subcutaneously. One hour before and 8 hours after the last PMSG administration ($d_{12}$), the animals receive the test compound in 0.1 ml of benzyl benzoate/castor oil (1:9) by subcutaneous injection. The control animals receive only the vehicle. The animals are sacrificed 24 hours after the final PMSG administration. Estradiol is analyzed in the serum by radioimmunology. For each group of 10 animals, the average value of estradiol concentration is calculated in nanomoles/liter with standard deviation. The stages of significance of the differences with respect to the control group are examined by variance analysis.

In order to determine the relative strength of efficacy of the compound to be tested as compared to the standard compound, the regression and covariance analysis is conducted. Furthermore, the percentage inhibition with respect to the PMSG control is calculated.

It is demonstrated, using as an example 15α-[(1R)acetoxy-2-methoxyethyl]-1-methylandrosta-1,4-diene-3,17-dione (B) according to the invention, that the compounds according to this invention lower the estradiol concentration in the serum to a far greater extent than the known 4-hydroxy-4-androstene-3,17-dione (A). Whereas inhibition of estradiol concentration is observed in case of the compounds of this invention at values as low as 2×0.03 mg, such inhibition occurs in case of the comparison compound only at 2×1.0 mg. A relative strength of efficacy of 6.3 is found for compound B as compared with compound A.

TABLE

Effect on Estradiol Concentration in Peripheral Serum of PMSG Pretreated Rats

| | Dose mg/Animal 2 × s.c. | n | Estradiol Concentration in nmol/l | Inhibition % | Relative Strength of Efficacy |
|---|---|---|---|---|---|
| PMSG Control | — | 10 | 6.21 ± 1.78 | — | — |
| | 0.3 | 10 | 4.10 ± 1.05 | 34 | |
| A | 1.0 | 10 | 2.38 ± 0.27 | 62 | 1.0 |
| | 3.0 | 10 | 0.81 ± 0.14 | 87 | |
| | 0.03 | 10 | 2.73 ± 0.51 | 56 | |
| B | 0.1 | 10 | 2.72 ± 0.51 | 56 | 6.3 |
| | 0.3 | 10 | 1.46 ± 0.25 | 76 | |
| | 1.0 | 10 | 0.62 ± 0.10 | 90 | | n = Number of animals per group

The compounds are inhibitors of estrogen biosynthesis (aromatase inhibitors). They are therefore suitable for the treatment of diseases caused by estrogen or diseases that are affected by estrogen. Thus, they are suitable for the treatment of estrogen-induced or -stimulated tumors, e.g., mamma carcinoma or prostate hyperplasia.

The compounds of this invention are also valuable for affecting fertility. Thus, male infertility resulting from increased estrogen levels can be cured by the novel active agents.

Furthermore, the compounds can be used as anti-fertility agents in women of childbearing age, in order to inhibit ovulation or implantation by estrogen withdrawal.

Aromatase inhibitors are likewise suitable for the treatment of impending myocardial infarction since elevated estrogen levels in the male can precede a cardiac infarction.

The amount of the compound to be administered fluctuates within a wide range and can cover any effective quantity. Depending on the condition to be treated and on the type of administration, the amount of compound administered can be 0.01–100 mg/kg body weight, preferably 0.1–20 mg/kg body weight, per day. The dosage is 0.01–100 mg/kg/day, preferably 0.01–20 mg/kg/day, analogous to the known agent aminoglutethimide when administered to treat estrogen-stimulated tumors, 0.01–100 mg/kg/day, preferably 0.1–20 mg/kg/day when administered analogous to the known agent aminoglutethimide to treat male infertility, 0.01–100 mg/kg/day, preferably 0.1–20 mg/kg/day when administered analogously to the known agent 4-hydroxy-4-androstene-3,17-dione to inhibit ovulation, and 0.1–30 mg/kg,day, preferably 0.1–20 mg/kg/day when administered analogously to the known agent 4-hydroxy-4-androstene-3,17-dione for the treatment of imminent myocardial infarction.

Capsules, pills, tablets, dragees, etc., can be utilized for oral administration. The dosage units can contain, besides the active ingredient, a pharmaceutically compatible carrier, e.g., amylose, sugar, sorbitol, gelatin, lubricant, silicic acid, talc, etc. The individual dosage units for oral administration can contain, for example, 10–100 mg of the active compound (as an aromatase inhibitor).

For parenteral administration, the active compounds can be dissolved or suspended in a physiologically compatible diluent. Very frequently, oils with or without the addition of a solubilizer, a surfactant, a suspending agent or an emulsifier are utilized as diluents. Examples for oils employed are olive oil, peanut oil, cottonseed oil, soybean oil, castor oil, and sesame oil.

The compounds can also be utilized in the form of a depot injection or an implantation preparation; these can be formulated so that timed release of active agent is made possible.

Implants can contain, as inert materials, for example biologically degradable polymers, or synthetic silicones, such as, for example, silicone rubber. The active compounds can furthermore be incorporated, for example into a plaster for percutaneous application.

Accordingly, the invention also concerns pharmaceutical preparations and the use of the novel compounds of Formula I for the manufacture of these preparations for the treatment of diseases linked to estrogen.

The invention also relates to a process for the production of compounds of Formula I, characterized by conventionally oxidizing 17-hydroxy steroids of Formula

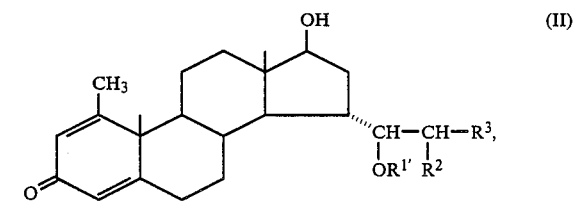

(II)

wherein $R^{1'}$ is a hydroxy blocking group or an acyl group of 1–10 carbon atoms, $R^2$ is an $OR^4$, an $NHR^5$ or an $S(O)_nR^6$ group, $R^4$ being a straight- or branched-chain alkyl group of 1–10 carbon atoms, $R^5$ being an acyl group of 1–10 carbon atoms, $R^6$ being a straight- or branched-chain alkyl group of 1–10 carbon atoms or an aryl group of 6–10 carbon atoms, $R^3$ is a hydrogen atom or a straight- or branched-chain alkyl group of 1–8 carbon atoms, and n is 0, 1 or 2, optionally splitting off the hydroxy blocking group, optionally saponifying the 15α-(1-alkanoyl group), and, if desired, esterifying the thus-obtained alcohol with a carboxylic acid of 1–10 carbon atoms.

The oxidation can be performed in a manner known per se, for example with chromic acid reagents (Jones reagent or chromic acid-pyridine) or with pyridinium dichromate or chlorochromate (J. Chem. Soc. 1953:2555; Tetrahedron Letters 1968:3363; Tetrahedron Letters 1979:399).

The hydroxy blocking groups represented by $R^{1'}$ in Formula II are groups that can be readily split off in an acidic medium, such as, for example, a tetrahydropyranyl, methoxymethyl or ethoxymethyl group.

Acyl groups can be saponified with an inorganic base in alcoholic solution. The following optional esterification is preferably carried out with the corresponding acid anhydride or halide in the presence of an organic base.

The starting material of Formula II is obtained by nucleophilic opening of 15α-(1,2-epoxyalkyl)-androstane prepared according to the directions of German Laid-Open Application P 35 39 244 (equivalent to U.S. application Serial No. 925,955 as noted above) and represented by Formula III

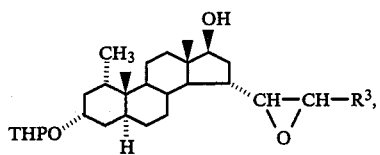

wherein R³ has the meanings given above, as well as after the secondary reactions likewise described therein (see also the experimental portion).

The nucleophilic epoxide opening is performed according to known methods (for example, Carl Djerassi, Steroid Reactions, San Francisco 1963:615; Weygand-/Hilgetag, "Organisch-chemische Experimentierkunst" [Art of Experimentation in Organic Chemistry], Leipzig 1970:667). Thus, introduction of the OR⁴ and, respectively, S(O)$_n$R⁶ substituent into the 15α-alkyl side chain takes place by opening the epoxides with alkali alcoholates and, respectively, alkali thioalcoholates at elevated temperatures. The resultant sulfides can be converted, by suitable oxidizing agents (e.g., hydrogen peroxide or peracids), into the desired sulfoxides (n=1) and, respectively, sulfones (n=2).

Compounds having an amino substituent in the 2 position of the 15α-alkyl side chain are obtained by heating the epoxides, in most cases for several hours, with alkali azides, such as, for example, sodium azide, in high-boiling, polar organic solvents, such as ethylene glycol, dimethylformamide, alcohols, e.g., methanol or ethanol, to temperatures of between about 35° and 200° C. and subsequent reduction of the thusformed azides (for example, by hydrogenation with palladium-calcium carbonate as a catalyst).

The amino-substituted compounds can also be produced by opening the epoxides with amines, for example in ethylene glycol by heating for several hours to about 100°-200° C. They are subsequently acylated, in accordance with methods likewise known in the literature.

Without further elaboration, it is believed that one skilled in the art can, using the preceding description; utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire text of all applications, patents and publications, if any, cited above and below are hereby incorporated by reference.

EXAMPLE 1

(a) 10.0 g of 17α-hydroxy-1α-methyl-15α-[(1R)-oxiranyl]-3α-tetrahydropyranyloxy-5α-androstane [German Laid-Open Application 35 39 244, Example 3(a)] is heated under reflux for 4 hours in 250 ml of methanol with 13.5 g of sodium methylate under argon gas. Subsequently, 14 ml of glacial acetic acid is added, the mixture is concentrated under vacuum, and the residue is dissolved in methylene chloride. After washing with sodium bicarbonate solution and with water, the mixture is concentrated by evaporation, thus obtaining 11.3 g of 17β-hydroxy-15α-[(1R)-hydroxy-2-methoxyethyl]-1α-methyl-3α-tetrahydropyranyloxy-5α-androstane.

(b) 11.3 g of 17β-hydroxy-15α-[(1R)-hydroxy-2-methoxyethyl]-1α-methyl-3α-tetrahydropyranyloxy-5α-androstane is stirred in 40 ml of pyridine and 20 ml of acetic anhydride for 16 hours at 20° C. The mixture is precipitated into ice water, suctioned off, washed, and dried, thus producing 12.87 g of amorphous 17β-acetoxy-15α-[(1R)-acetoxy-2-methoxyethyl]-1α-methyl-3α-tetrahydropyranyloxy-5α-androstane; this product is heated under reflux for 2 hours in 200 ml of 2-propanol and 50 ml of water with 2.5 g of oxalic acid. After evaporation under vacuum, the residue is dissolved in methylene chloride, washed neutral, and the solvent removed by distillation. An amount of 11.48 g of the thus-obtained 3α-hydroxy compound is stirred in 100 ml of acetone with 25 ml of Jones reagent for 10 minutes under water cooling. The mixture is precipitated thereafter into water and worked up. Recrystallization from hexane/acetone yields 7.5 g of 17βacetoxy-15α-[(1R)-acetoxy-2-methoxyethyl]-1α-methyl-5α-androstan-3-one, mp 149°-150° C.

(c) 7.17 g of 17β-acetoxy-15α-[(1R)-acetoxy-2-methoxyethyl]-1α-methyl-5α-androstan-3-one is dissolved in 95 ml of glacial acetic acid and, under cooling to 15° C., a solution of 38.75 ml of bromine in glacial acetic acid (prepared from 2.26 ml of bromine in 50 ml of glacial acetic acid) is added dropwise within 10 minutes and further stirred for 10 minutes. After precipitation into ice water, the mixture is suctioned off, washed neutral and dried. 10.9 g of crude 2,4-dibromo compound is combined in 100 ml of dimethylformamide with 10.0 g of lithium carbonate and agitated for 2 hours at a bath temperature of 140° C. After precipitation into water, working up, and recrystallization from acetone/hexane, 4.28 g of 18β-acetoxy-15α-[(1R)-acetoxy-2-methoxyethyl]-1-methylandrosta-1,4-dien-3-one is obtained, mp 187°-188° C.

(d) 3.35 g of 17β-acetoxy-15α-[(1R)-acetoxy-2-methoxyethyl]-1-methylandrosta-1,4-dien-3-one is stirred in 60 ml of methanol with 2 ml of 3% strength potassium hydroxide solution in methanol at room temperature for 4.5 hours. After neutralization with acetic acid, working up, chromatography on silica gel, and recrystallization from acetone/hexane, 1.3 g of 17β-hydroxy-15α-[(1R)-acetoxy-2-methoxyethyl]-1-methylandrosta-1,4-dien-3-one is obtained, mp 203°-204° C.

(e) 890 mg of 17β-hydroxy-15α-[(1R)-acetoxy-2-methoxyethyl]-1-methylandrosta-1,4-dien-3-one is dissolved in 30 ml of acetone, combined with 2.5 ml of Jones reagent, and stirred for 45 minutes at room temperature. After working up, chromatography on silica gel, and recrystallization from acetone/hexane, 763 mg of 15α-[(1R)-acetoxy-2-methoxyethyl]-1-methylandrosta-1,4-diene-3,17-dione is obtained, mp 184°-185° C.

EXAMPLE 2

Analogously to the directions given in Example 1, 15α-[(1R)-acetoxy-2-ethoxyethyl]-1-methylandrosta-1,4-diene-3,17-dione is obtained, mp 155°-157° C.

EXAMPLE 3

(a) 36.0 g of 15α-propenyl-17β-hydroxy-1α-methyl-3α-tetrahydropyranyloxy-5α-androstane (German Laid-Open Application 35 39 244, Example 15a) is dissolved in 900 ml of ethylene chloride, combined with 63.0 g of p-nitroperbenzoic acid, and stirred for one hour at 0°–5° C. After dilution with methylene chloride, the mixture is washed with 1-molar sodium hydroxide solution and with water, and evaporated under vacuum. By chromatography on silica gel and crystallization from ether-pentane, 27.7 g of 17β-hydroxy-15α-(1,2-epoxypropyl)-1α-methyl-3α-tetrahydropyranyloxy-5α-androstane is produced, mp 172°–174° C.

(b) Under argon, 26.5 g of epoxide is stirred in 550 ml of ethylene glycol with 39.5 g of sodium azide for one hour at a bath temperature of 180° C. Subsequently, the mixture is precipitated into ice water, suctioned off, washed with water, and dried. Chromatography on silica gel yields 20.6 g of 17β-hydroxy-15α-[(1R)hydroxy-(2R)-azidopropyl]-1α-methyl-3α-tetrahydropyranyloxy-5α-androstane, mp 183°–184° C; and 4.5 g of 17β-hydroxy-15α-[(1R)-hydroxy-(2S)-azidopropyl]-1α-methyl-3α-tetrahydropyranyloxy-5α-androstane, mp 141°–143° C.

(c) 20.6 g of 17β-hydroxy-15α-[(1R)-hydroxy-(2R)azidopropyl]-1α-methyl-3α-tetrahydropyranyloxy-5α-androstane is hydrogenated in 500 ml of methanol with 2.0 g of 10% palladium-calcium carbonate. The catalyst is filtered off and the methanol removed by distillation. An amount of 21.0 g of crude amino compound is allowed to stand for 16 hours at room temperature with 80 ml of pyridine and 40 ml of acetic anhydride. After precipitation into water, the mixture is suctioned off, washed with water, and dried. The crude product is chromatographed on silica gel, thus obtaining 24.4 g of 17β-acetoxy-15α-[(1R)-acetoxy-(2R)-acetylaminopropyl]-1α-methyl-3α-tetrahydropyranyloxy-5α-androstane.

(d) 24.4 g of 17β-acetoxy-15α-[(1R)-acetoxy-(2R)acetylaminopropyl]-1α-methyl-3α-tetrahydropyranyloxy-5α-androstane is heated under reflux in 500 ml of methanol and 125 ml of water with 6.5 g of oxalic acid for 10 minutes. After working up of the mixture, 20.3 g of crude 3α-hydroxy compound is obtained which is oxidized in 250 ml of acetone with 14 ml of Jones reagent. After working up and recrystallization from methylene chloride-isopropyl ether, 17.2 g of 17β-acetoxy-15α-[(1R)-acetoxy-(2R)-acetylaminopropyl]-1α-methyl-5α-androstan-3-one is obtained, mp 232°–234° C.

(e) 16.2 g of 17β-acetoxy-15α-[(1R)-acetoxy-(2R)-acetylaminopropyl]-1α-methyl-5α-androstan-3-one is brominated and dehydrobrominated as described in Example 1(c). After chromatography of the crude product and recrystallization from methylene chloride-isopropyl ether, 7.35 g of 17β-acetoxy-15α-[(1R)-acetoxy-(2R)-acetylaminopropyl]-1-methylandrosta-1,4-dien-3-one is obtained, mp 249°–251° C.

(f) 5.1 g of 17β-acetoxy-15α-[(1R)-acetoxy-(2R)acetylaminopropyl]-1-methylandrosta-1,4-dien-3-one is agitated in 100 ml of 0.1% strength potassium hydroxide solution in methanol at room temperature for 5 hours. The mixture is neutralized with acetic acid and worked up. The crude product is chromatographed on silica gel. Elution with tert-butylmethyl ether-methanol (8:2) yields 1.88 g of 17β-acetoxy-15α-[(1R)-hydroxy-(2R)-acetylaminopropyl]-1-methylandrosta-1,4-dien-3-one; this product is stirred in 6 ml of tetrahydrofuran and 3 ml of dihydropyran, after addition of 0.03 g of p-toluenesulfonic acid, for 15 hours at 20° C. After working up, 2.6 g of 17β-acetoxy-15α-[(1R)-tetrahydropyranyloxy-(2R)acetylaminopropyl]-1-methylandrosta-1,4-dien-3-one is obtained which is stirred for one hour at 20° C. in 50 ml of 1% strength potassium hydroxide solution. After working up and chromatography, 2.05 g of 17β-hydroxy-15α-[(1R)-tetrahydropryanyloxy-(2R)acetylaminopropyl]-1-methylandrosta-1,4-dien-3-one is isolated.

(g) 1.8 g of 17β-hydroxy-15α-[(1R)-tetrahydropyranyloxy(2R)-acetylaminopropyl]-1-methylandrosta-1,4-dien-3-one is oxidized in 50 ml of methylene chloride with 5.2 g of pyridinium dichromate for 15 hours at room temperature. The mixture is precipitated into ice water, suctioned off, and dried. An amount of 1.45 g of the thus-obtained 17-ketone is heated under reflux for 40 minutes in 24 ml of methanol and 6 ml of water with 300 mg of oxalic acid. After working up and chromatography, 1.1 g of 15α-[(1R)hydroxy-(2R)-acetylaminopropyl]-1-methylandrosta1,4-diene-3,17-dione is isolated. 960 mg of the above compound is reacted in 4 ml of pyridine and 2 ml of acetic anhydride and worked up. Recrystallization from acetone-hexane yields 945 mg of 15α-[(1R)-acetoxy-(2R)-acetylaminopropyl]-1-methylandrosta-1,4-diene-3,17-dione, mp 251-253° C.

EXAMPLE 4

4.5 g of 17β-hydroxy-15α-[(1R)-hydroxy-(2S)-azidopropyl]1α-methyl-3α-tetrahydropyranyloxy-5α-androstane [Example 3(b)] is reacted as described in Examples 3(c)3(g). Recrystallization from acetone-ether yields 190 mg of 15α-[(1R)-acetoxy-(2S)-acetylaminopropyl]-1-methylandrosta-1,4-diene-3,17-dione, mp 179-180° C.

EXAMPLE 5

17β-Hydroxy-1α-methyl-15α-[(1R)-oxiranyl]-3α-tetrahydropyranyloxy-5α-androstane [German Laid-Open Application 35 39 244, Example 3(a)] is reacted as described in Example 3, thus obtaining the amorphous 15α-[(1R)acetoxy-2-acetylaminoethyl]-1-methylandrosta-1,4-diene-3,17-dione.

EXAMPLE 6

(a) 5 g of 17β-hydroxy-1α-methyl-15α-[(1R)-oxiranyl]-3α-tetrahydropyranyloxy-5α-androstane [German Laid-Open Application 35 39 244, Example 3(a)] is combined in 100 ml of ethylene glycol with 7.0 g of sodium thiomethylate (prepared from 4.8 g of methanethiol and 2.4 g of sodium hydride) and heated for 3 hours to 100° C. Then the mixture is worked up as in Example 3(b) and chromatographed, thus isolating 2.1 g of 17β-hydroxy-15α-[(1R)-hydroxy-(2R)methylthioethyl]1α-methyl-3α-tetrahydropyranyloxy-5α-androstane.

(b) 2.0 g of the sulfide produced according to 6(a) is dissolved in 100 ml of acetonitrile and combined at 50° C. within 2 hours with a solution of 5.2 g of sodium metaperiodate in 30 ml of water. Then the mixture is diluted with ice water, the crystals are suctioned off, washed with water, and dried. After chromatography on silica gel, 1.06 g of 2-(17β-hydroxy-1α-methyl-3α-tetrahydropyranyloxy-5α-androstan-15α-yl]-2-hydroxyethylmethyl sulfoxide is obtained as a mixture of diastereomers.

(c) The sulfoxide.prepared according to (b) is acetylated as described in Example 3(c) and further reacted in analogy to the directions in Examples 3(d) through 3(g), thus isolating 105 mg of 2-acetoxy-2(1-methylandrosta-1,4-diene-3,17-dion-15α-yl)ethylmethyl sulfoxide.

EXAMPLE 7

(a) 2.0 g of the sulfoxide prepared according to Example 6(b) is dissolved in 80 ml of dimethoxyethane and combined under ice cooling with 5 ml of 30% strength peracetic acid. Then the mixture is diluted with ice water, the crystals are filtered off, rinsed with water, and dried. The crystals are chromatographed on silica gel, thus isolating 1.2 g of 2-(17β-hydroxy-1α-methyl-3α-tetrahydropyranyloxy-5α-androstan-15α-yl)-2-hydroxyethylmethylsulfone.

(b) The sulfone prepared according to (a) is acetylated as described in Example 3(c) and further reacted analogously to the directions in Examples 3(d) through 3(g), thus isolating 120 mg of 2-acetoxy-2-(1-methylandrosta-1,4-diene-3,17-dion-15α-yl)ethylmethylsulfone.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. 1-Methyl-15α-(1-oxyalkyl)androsta-1,4-diene-3,17-diones of the formula

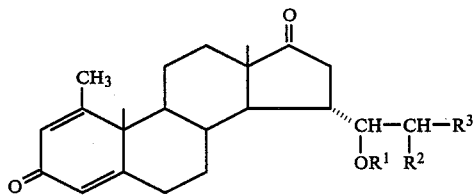

wherein $R^1$ is H or $C_{1-10}$-alkanoyl, $R_2$ is $OR^4$, $NHR^5$ or $S(O)_nR^6$, $R^4$ being $C_{1-10}$ alkyl, $R^5$ being a $C_{1-10}$-alkanoyl, $R^6$ being $C_{1-10}$-alkyl or $C_{6-10}$-aryl, $R^3$ is H or $C_{1-8}$-alkyl and n is 0, 1 or 2.

2. A compound according to claim 1, wherein $R^1$ is acetyl, propionyl, isopropionyl or butyryl.

3. A compound according to claim 2, wherein $R^1$ is acetyl.

4. A compound according to claim 3, wherein $R^2$ is $OR^4$.

5. A compound according to claim 4, wherein $R^4$ is methyl or ethyl.

6. A compound according to claim 3, wherein $R^2$ is $NHR^5$.

7. A compound according to claim 6, wherein $R^5$ is acetyl.

8. A compound according to claim 3, wherein $R^2$ is $S(O)_nR^6$.

9. A compound according to claim 8, wherein $R^6$ is methyl and n is 1.

10. A compound according to claim 8, wherein $R^6$ is methyl and n is 2.

11. A compound according to claim 1, wherein $R^3$ is methyl, ethyl, propyl, butyl, isobutyl or pentyl.

12. A compound according to claim 1, wherein $R^2$ is $OR^4$ and $R^4$ is methyl, ethyl, propyl or isopropyl.

13. A compound according to claim 1, wherein $R^2$ is $NHR^5$ and $R^5$ is acetyl, propionyl or isobutyryl.

14. A compound according to claim 1, wherein $R^2$ is $S(O)_nR^6$ and $R^6$ is methyl, ethyl, propyl, isopropyl, phenyl, toluyl or naphthyl.

15. A compound of claim 1, which is
15α-[(1R)-Acetoxy-2-methoxyethyl]-1-methylandrosta-1,4-diene-3,17-dione,
15α-[(1R)-Acetoxy-2-ethoxyethyl]-1-methylandrosta-1,4-diene-3,17-dione,
15α-[(1R)-Acetoxy-(2R)-acetylaminopropyl]-1-methylandrosta-1,4-diene-3,17-dione,
15α-[(1R)-Acetoxy-(2S)-acetylaminopropyl]-1-methylandrosta-1,4-diene-3,17-dione,
15α-[(1R)-Acetoxy-2-acetylaminoethyl]-1-methylandrosta-1,4-diene-3,17-dione,
2-Acetoxy-2-(1-methylandrosta-1,4-diene-3,17-dion-15α-yl)ethylmethyl sulfoxide, or
2-Acetoxy-2-(1-methylandrosta-1,4-diene-3,17-dion-15α-yl)ethylmethylsulfone.

16. A pharmaceutical composition comprising a compound of claim 15 and a pharmaceutically acceptable carrier.

17. A pharmaceutical composition comprising a compound of claim 1 and a pharmaceutically acceptable carrier.

18. A method of inhibiting estrogen biosynthesis in a host in need of such inhibition comprising administering an effective amount of a compound of claim 1.

19. A method according to claim 18, wherein the amount is 10–100 mg.

20. A method of treating mamma carcinoma or prostate hyperplasia in a patient, in need of such treatment comprising administering an effective amount of a compound of claim 1.

* * * * *